United States Patent
Brunner et al.

(10) Patent No.: US 12,041,950 B2
(45) Date of Patent: *Jul. 23, 2024

(54) STORAGE STABLE MIXTURES

(71) Applicant: DSM IP ASSETS B.V., Heerlen (NL)

(72) Inventors: Dominik Josef Brunner, Kaiseraugst (CH); Laure Clasadonte, Kaiseraugst (CH); Martin Reto Gadient, Kaiseraugst (CH); Roland Schuepfer, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 659 days.

This patent is subject to a terminal disclaimer.

(21) Appl. No.: 16/770,996

(22) PCT Filed: Dec. 17, 2018

(86) PCT No.: PCT/EP2018/085191
§ 371 (c)(1),
(2) Date: Jun. 9, 2020

(87) PCT Pub. No.: WO2019/121508
PCT Pub. Date: Jun. 27, 2019

(65) Prior Publication Data
US 2020/0367529 A1 Nov. 26, 2020

(30) Foreign Application Priority Data

Dec. 18, 2017 (EP) .................................. 17207905

(51) Int. Cl.
| | | |
|---|---|---|
| *A23K 20/105* | (2016.01) | |
| *A23K 20/158* | (2016.01) | |
| *A23K 20/24* | (2016.01) | |
| *A23K 20/28* | (2016.01) | |
| *A23K 50/10* | (2016.01) | |

(52) U.S. Cl.
CPC .......... *A23K 20/105* (2016.05); *A23K 20/158* (2016.05); *A23K 20/24* (2016.05); *A23K 20/28* (2016.05); *A23K 50/10* (2016.05)

(58) Field of Classification Search
CPC .... A23K 20/105; A23K 20/158; A23K 20/24; A23K 20/28; A23K 50/10; A23K 20/20; A23K 20/22; Y02P 60/22; A61K 9/0056; A61K 9/143; A61K 9/145; A61K 31/047
See application file for complete search history.

(56) References Cited

U.S. PATENT DOCUMENTS

2015/0272167 A1* 10/2015 Varner .................. A23K 10/37
426/1

FOREIGN PATENT DOCUMENTS

| WO | 2012/084629 | 6/2012 |
| WO | WO 2019/007740 | 1/2019 |

OTHER PUBLICATIONS

Guyader et al., "Redirection of Metabolic Hydrogen by Inhibiting Methanogenesis in the Rumen Simulation Technique (RUSITEC)," Frontiers in Microbiology, Mar. 2017, vol. 8, Article 393, pp. 1-16.
Romero-Perez et al., "Sustained reduction in methane production from long-term addition of 3-nitrooxypropanol to a beef cattle diet," Journal of Animal Science, 2015.93:1780-1791.
Haisan et al., "The effects of feeding 3-nitrooxypropanol on methane emissions and productivity of Holstein cows in mid lactation," Journal of Dairy Science, vol. 97, No. 5, 2014, pp. 3110-2119.
Jelisavac et al., "Analysis of the Aging Process of Double-Base Propellants Without an Organic Stabilizer," Scientific Technical Review, 2014, vol. 64, No. 3, pp. 3-9.
Duin et al., "Mode of action uncovered for the specific reduction of methane emissions from ruminants by the small molecule 3-nitrooxypropanol," PNAS, May 31, 2016, vol. 113, No. 22, pp. 6172-6177.
International Search Report for PCT/EP2018/085191, mailed Feb. 4, 2019, 3 pages.
Written Opinion of the ISA for PCT/EP2018/085191, mailed Feb. 4, 2019, 12 pages.
Guyader et al., "Redirection of Metabolic Hydrogen by Inhibiting Methanogenesis in the Rumen Simulation Technique (RUSITEC)", Frontiers in Microbiology, Mar. 14, 2017, vol. 8, article 393, XP055447683, pp. 1-16.
Romero-Perez et al., "Sustained reduction in methane production from long-term addition of 3-nitrooxypropanol to a beef cattle diet", Journal of Animal Science, 2015, vol. 93, pp. 1780-1791.
Haisan et al., "The effects of feeding 3-nitrooxypropanol on methane emissions and productivity of Holstein cows in mid lactation", Journal of Dairy Science, May 1, 2014, vol. 97, pp. 3110-3119.
Communication pursuant to Article 94(3) EPC, EP Application No. 18815760.6, Jun. 4, 2024.

* cited by examiner

*Primary Examiner* — Jessica Worsham
(74) *Attorney, Agent, or Firm* — NIXON & VANDERHYE P.C.

(57) ABSTRACT

The present invention relates to improved formulations of propandiol mononitrate and derivatives thereof as well as to the production of such formulations.

15 Claims, No Drawings

STORAGE STABLE MIXTURES

This application is the U.S. national phase of International Application No. PCT/EP2018/085191 filed 17 Dec. 2018, which designated the U.S. and claims priority to EP Patent Application No. 17207905.5 filed 18 Dec. 2017, the entire contents of each of which are hereby incorporated by reference.

The present invention relates to storage stable mixtures comprising propandiol propanediol mononitrate and derivatives thereof as well as to the production and use of such forms.

The temperature of the air surrounding the earth is increasing, a process referred to as global warming. One of the main focuses to reduce this warming effect is to reduce the amount of greenhouse gases emitted into the atmosphere. Greenhouse gases are emitted from several different sources, both natural and artificial; however, the two sources with the most emphasis are the agricultural and fossil fuel industries. Within agriculture, ruminants and in particular cattle are the major contributors to the biogenic methane formation, and it has been estimated that the prevention of methane formation from ruminants would almost stabilize atmospheric methane concentrations.

1,3-Propanediol mononitrate (in the following referred to as propanediol mononitrate, respectively PDMN) and derivatives thereof have been reported to be highly efficient in reducing the formation of methane in ruminants without affecting microbial fermentation in a way that would be detrimental to the animal (WO2012/084629).

However, comprising propanediol mononitrate and derivatives thereof have been found not to be effectively retained under conventional storage conditions, in particular when absorbed onto standard carrier systems commonly used in the feed industry. Furthermore, it has been found that the incorporation of comprising propanediol mononitrate absorbed on silica into standard pre-mixes even further reduces the storage stability. The lack of retention of the active is, how-ever, highly unwanted as accordingly an appropriate dosage is not possible without undue burden, i.e. sophisticated packaging, analysis of the active content before use or overdosing. Moreover, all these methods add significant additional costs-in-use which are not readily accepted by the end user.

Thus, there is an ongoing need for product forms and methods, which overcome the above-mentioned problems by enabling the storage over a period of time without significant losses of the active, i.e. of propanediol mononitrate respectively derivatives thereof.

Surprisingly, it has now been found that the addition of an inorganic carbonate to a powderous formulation of propanediol mononitrate absorbed onto silica, also after incorporation thereof into a mineral premix significantly increased the retention of propanediol mononitrate.

Thus, in a first embodiment the present invention relates to a storage stable mixture (1) comprising
  (a1) a powderous formulation (A) comprising
    (i) a compound of formula (I)

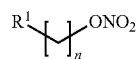

formula (I)

wherein
n is an integer from 1 to 15

$R^1$ is selected from the group consisting of H, $C_1$-$C_6$alkyl, phenyl, —OH, —$NH_2$, —CN, —COOH, —O(C=O)$R^8$, —NHC(=O)$R^8$, $SO_2NHR^8$, and —$ONO_2$, and $R^8$ is $C_1$-$C_6$alkyl, phenyl, pyridyl such as preferably 2-pyridyl with the proviso that when n is >3 the hydrocarbon chain may be interrupted by —O— or —NH—, and
    (ii) silica, and
  (a2) at least one inorganic carbonate.

In a preferred embodiment, the amount of the powderous formulation (A) in the storage stable mixture (I) is at least 5 wt.-%, more preferably at least 10 wt.-%, based on the total weight of the storage stable mixture (I). More preferably, the amount of the powderous formulation (A) in the storage stable mixture (I) is selected in the range from 5 to 85 wt.-%, most preferably in the range from 5 to 60 wt.-%, such as in the range of 5 to 50 wt.-%, based on the total weight of the storage stable mixture (I).

In a further preferred embodiment, the amount of the at least one inorganic carbonate (total) in the storage stable mixture (I) is at least 10 wt.-%, more preferably at least 20 wt.-%, most preferably at least 50 wt.-%, based on the total weight of the storage stable mixture (I). More preferably, the amount of the at least one inorganic carbonate in the storage stable mixture (I) is selected in the range from 15 to 95 wt.-%, most preferably in the range from 40 to 95 wt.-%, such as in the range of 50 to 95 wt.-%, based on the total weight of the storage stable mixture (I).

The term 'storage-stable' as used herein refers to an improved retention of the compound of formula (I) in the mixture according to the present invention compared to the respective mixture without the at least one inorganic carbonate. Preferably, the retention is improved by at least 10%, more preferably by at least 20%, most preferably by at least 30% compared to the respective mixture without any inorganic carbonate.

In all embodiments of the present invention the weight-ratio (w/w) of the at least one inorganic carbonate (total) to the powderous formulation is preferably selected in the range of 50:1 to 1:5, preferably in the range of 40:1 to 1:2, most preferably in the range of 30:1 to 1:1 or 20:1 to 1:1.

In another preferred embodiment of the present invention, the weight-ratio (w/w) of the inorganic carbonate to the powderous formulation is at least 1, preferably at least 5, more preferably at least 10, most preferably at least 15, such as e.g. at least 25 or at least 50.

In all embodiments of the present invention, preferably the weight-ratio (w/w) of the inorganic carbonate to the compound of formula (I) is at least 1:1, preferably at least 5:1, more preferably at least 10:1, and most preferably at least 25:1 such as at least 50:1.

Even more advantageously in all embodiments of the present invention the weight-ratio (w/w) of the inorganic carbonate to the compound of formula (I) is selected in the range of 200:1 to 1:1 (i.e. 200 parts of inorganic carbonate to 1 part of a compound of formula (I) to 1 parts of inorganic carbonate to 1 part of a compound of formula (I)), more preferably in the range of 150:1 to 5:1, most preferably in the range of 100:1 to 10:1 such as particularly 100:1 to 25:1. Further suitable ranges are 100:1 to 15:1, 100:1 to 30:1 or 100:1 to 35:1, 100:1 to 50:1 as well as 100:1 to 75:1.

The term 'powderous formulation' as used herein refers to solid formulations in powder form which freely flow (i.e. free flowing powders).

The amount of silica in the powderous formulations according to the present invention is generally selected in the range of 25 to 90 wt.-%, such as in the range of 30 to 90 wt.-%, 35 to 90 wt.-% or 40 to 90 wt.-%.

In all embodiments of the present invention the powderous formulation (A) is preferably a powderous formulation (B) comprising
  (i) at least 0.1 wt-%, based on the total weight of the powderous formulation, of a compound of formula (I), and
  (ii) at least 25 wt-%, based on the total weight of the powderous formulation, of silica, and
  (iii) 0 to 40 wt-%, based on the total weight of the powderous formulation, of an edible oil.

The term 'edible oil' refers to oils commonly used in feed applications. Preferred edible oils to be used in the powderous formulations according to the present invention are propyleneglycol, canola oil, corn oil, rapeseed oil, sunflower oil, middle chain triglyceride (MCT), soy bean oil and glycerol as well as mixtures thereof. The most preferred edible oil to be used in the powderous formulation according to the present invention is propyleneglycol.

The powderous formulations according to the present invention may furthermore contain small amounts of customary additives commonly used in the preparation of powderous formulations for feed application.

Therefore, in a further embodiment the present invention relates to powderous formulations (B) which are powderous formulations (C) which further comprise (iv) 0 to 10 wt-%, based on the total weight of the formulation, of an additive.

The powderous formulation according to the present invention are generally prepared by a process wherein the compound of formula (I) is, optionally diluted in the edible oil and further optionally admixed with the additive(s), sprayed onto or admixed with a silica.

Alternatively, the powderous formulations according to the present invention can be prepared by a process wherein the compound of formula (I) is, optionally in the presence of the edible oil and further optionally admixed with the additive(s), diluted in an organic solvent suitable for the preparation of feed products such as e.g. dichloromethane which dilution is then sprayed onto or admixed with silica followed by evaporation of the organic solvent.

In a particular advantageous embodiment, the powderous formulations according to the present invention are adsorbates.

For the purposes of the present invention, adsorbates are, in particular, preparations in which at least 10 wt.-%, in particular at least 20 wt.-%, preferably at least 30 wt.-%, particularly preferably at least 40 wt.-%, in particular at least 50 wt.-% of the components to be adsorbed (i.e. all constituents of the adsorbate without the silica, i.e. the compound(s) of formula (I), and optionally the edible oil and the additives) are present in the internal pore volume of the silica. The internal pore volume of a carrier can be determined as void volume by the DPB (dibutyl phthalate) method DIN 53601.

Particular preference is given to adsorbates of which at least 60 wt.-%, preferably at least 70 wt.-%, in particular at least 80 wt.-%, is present in the internal pore volume of the silica.

Silica is a well-known carrier material in the feed and food industry and refers to white microspheres of amorphous silica (also referred to as silicone dioxide) and is available in a great variety of particle sizes. Particular suitable silica to be used in powderous formulations according to the present invention is amorphous precipitated silica e.g. available as Ibersil D-250 at IQE Group, Sipernat 2200 at Evonik or Tixosil 68 at Solvay, Zeofree 5170 from J.M. Huber Cooperation or Newsil $C_{50}$ from Quechen Silicon Chemical Co Ltd.

Preferably the silica which is used in powderous formulations according to the present invention has an average particle size D(v, 0.5)>200 µm. More preferably the particle size of the silica is selected in the range of 200 µm to 400 µm, most preferably in the range of 250 µm to 380 µm, even more preferably in the range of 300 to 360 µm.

The particle sizes as given herein are measured by a Malvern Master Sizer 2000 following the recommendations outlined in ISO13320-1 for particle size analysis via laser diffraction methods (laser diffraction light scattering). During this laser diffraction measurement, particles are passed through a focused laser beam. The particles scatter light at an angle that is inversely proportional to their size. The angular intensity of the scattered light is then measured by a series of photosensitive detectors. The map of scattering intensity versus angle is the primary source of information used to calculate the particle size. For the measurement of the silica according to the present invention a dry powder feeder (Malvern Scirocco) was used.

Advantageously, the silica which is used in the powderous formulations according to the present invention furthermore exhibits a pH in the range of pH 6 to 8.5 (measured as a 1% suspension in distillated water), such as preferably in the range of pH 7 to 8.

The term 'additive' as used herein refers to additives commonly used in the preparation of powderous formulations for feed application. Preferred additives to be used in the powderous formulations according to the present invention are thickeners, such as in particular gums or cellulose derivatives such as xanthan gum, karaya gum and/or ethylcellulose.

Particular advantageous powderous formulations according to the present invention are powderous formulation (A) which are powderous formulations (D) consisting essentially of
  (i) 1 to 25 wt-%, based on the total weight of the powderous formulation, of a compound of formula (I), and
  (ii) at least 20 wt-%, based on the total weight of the powderous formulation, of silica, and
  (iii) 5 to 45 wt-%, based on the total weight of the formulation, of at least one edible oil, and
  (iv) 0 to 10 wt-%, based on the total weight of the powderous formulation, of an additive.

Even more advantageous powderous formulations according to the present invention are powderous formulations (A) which are powderous formulations (E) consisting essentially of (i) 2 to 20 wt-%, based on the total weight of the powderous formulation, of a compound of formula (I), and
  (ii) at least 25 wt-%, based on the total weight of the powderous formulation, of silica, and
  (iii) 10 to 45 wt-%, based on the total weight of the powderous formulation, of an edible oil, and
  (iv) 0 to 10 wt-%, based on the total weight of the powderous formulation, of an additive.

An especially preferred powderous formulation according to the present invention is a powderous formulation (A) which is a powderous formulations (F) consisting essentially of
  (i) 2 to 15 wt-%, based on the total weight of the powderous formulation, of a compound of formula (I), and (ii) at least 40 wt-%, based on the total weight of the powderous formulation, of silica, and (iii) 20 to 40 wt-%, based on the total weight of the powderous formulation, of an edible oil, and (iv) 0 to 5 wt-%, based on the total weight of the powderous formulation, of an additive.

The compounds of formula (I) preferably have a boiling point below 250° C. at 760 Torr, preferably a boiling point in the range of 100 and 200° C. at 760 Torr.

The compounds of formula (I) are known and either commercially available or can be prepared in analogy to the processes as e.g. disclosed in WO2012/084629.

Particular advantageous compounds of formula (I) to be used in the powderous formulations according to the present invention are the compounds wherein n is an integer between 3 and 9 and $R^1$ is OH, COOH or —$ONO_2$ and with the proviso that if n is 4 the hydrocarbon chain may be interrupted by —NH— such as in particular the compounds of formula $R^1$—$(CH_2)_2$—NH—$(CH_2)_2$—$ONO_2$. Even more preferred are compounds of formula (I) wherein n is an integer between 3 and 9 and $R^1$ is OH, COOH or —$ONO_2$.

Even more advantageous compounds of formula (I) to be used in the powderous formulations according to the present invention are propanediol mononitrate (CAS-No: 100502-66-7), 9-nitrooxynonanol, 5-nitroxy pentanoic acid (CAS 74754-56-6), 6-nitroxy hexanoic acid (CAS 74754-55-5), bis(2-hydroxyethyl)amine dinitrate (CAS 20830-49-3), 1,4-bis-nitrooxybutane (CAS 3457-91-8) and 1,5-bis-nitrooxypentane (CAS 3457-92-9). The most preferred compound of formula (I) to be used in the powderous formulations according to the present invention is propanediol mononitrate.

Thus, a very specific powderous formulation according to the present invention is a powderous formulation (A) which is a powderous formulations (G) consisting essentially of (i) 2 to 15 wt-%, based on the total weight of the powderous formulation, of propanediol mononitrate, and (ii) at least 45 wt-%, based on the total weight of the powderous formulation, of silica, and (iii) 20 to 40 wt-%, based on the total weight of the powderous formulation, of propyleneglycol.

The term 'powderous formulation consisting essentially of' indicates that the addition of all wt-% of the listed ingredients of the powderous formulations adds up to 100 wt.-% (i.e. the amount of silica is adjusted accordingly) with the proviso, however, that it cannot be excluded that small amount of impurities or water (moisture) may be present in the powderous formulations according to the present invention such as e.g. in amounts of less than 7 wt.-%, preferably less than 5 wt.-%, more preferably less than 3 wt.-%, which impurities/water (moisture) are introduced via the respective raw materials or processes used and which are not added separately.

The powderous formulations (A) to (G) with all the preferences and definitions as given herein can additionally be coated with customary coatings in the art such as wax or fats. If present, such coating is generally applied in amounts of 5 to 50 wt.-% based on the total weight of the powderous form. Advantageously, the coating comprises at least one wax and/or at least one fat, which has a dropping point (Tropfpunkt) of from 30 to 85° C.

The dropping point of a material as used herein refers to the temperature (in ° C.) when the material begins to melt under standardized conditions. Thus, the material is heated so long until it changes the state of matter from solid to liquid. The dropping point is the temperature when the first dropping is released from the material. The determination of the dropping point is carried out as described in the standard norm DIN ISO 2176.

Particularly suitable waxes to be used as coating in the context of the present invention include organic compounds consisting of long alkyl chains, natural waxes (plant, animal) which are typically esters of fatty acids and long chain alcohols as well as synthetic waxes, which are long-chain hydrocarbons lacking functional groups.

Particularly suitable fats to be used as coating in the context of the present invention include a wide group of compounds which are soluble in organic solvents and largely insoluble in water such as hydrogenated fats (or saturated fats) which are generally triesters of glycerol and fatty acids. Suitable fats can have natural or synthetic origin. It is possible to hydrogenate a (poly)unsaturated fat to obtain a hydrogenated (saturated) fat.

Preferred examples of waxes and fats to be used as coating according to the present invention are glycerine monostearate, carnauba wax, candelilla wax, sugarcane wax, palmitic acid, stearic acid hydrogenated cottonseed oil, hydrogenated palm oil and hydrogenated rapeseed oil as well as mixtures thereof.

In a preferred embodiment, the powderous formulations (A) to (G) with all the preferences and definitions as given herein are not coated.

The term 'inorganic carbonate' according to the present invention refers to any inorganic carbonate suitable for feed application (inorganic feed carbonate) such as preferably the alkaline and earth alkaline salts of carbonate, more preferably calcium carbonate, magnesium carbonate, sodium hydrogencarbonate.

Particular preferred in all embodiments of the present invention are sodium bicarbonate and/or calcium carbonate (in pure form or as limestone). Most preferred in all embodiments of the present invention is the use of sodium bicarbonate and/or limestone.

Commercially available inorganic carbonate grades suitable for the purpose of the present invention are e.g. limestone commercially available as Animal Feed Lime at Bennettsbridge or sodium bicarbonate which is e.g. commercially available as FEED GRADE SODIUM BICARBONATE (containing not less than 99% of sodium bicarbonate) at Natural Soda Inc.

It is well understood, that the storage stable mixtures (1) according to the present invention may contain additional active and/or feed ingredients and/or edible oils conventionally used in the feed industry and/or in feed products.

Thus, in a further embodiment, the present invention relates to a storage stable mixture (1) with all the definitions and preferences as given herein which is a storage stable mixture (2) further comprising (a3) at least one active ingredient and/or at least one feed ingredient and optionally (a4) at least one edible oil.

In a particular advantageous embodiment, the storage stable mixture (1) is a storage stable mixture (3) comprising (a1) a powderous formulation (A), (B), (C), (D), (E), (F) or (G), and (a2) at least one inorganic carbonate, and (a3) at least one active ingredient and/or at least one feed ingredient, and optionally (a4) at least one edible oil.

In a particular preferred embodiment, the at least one active ingredient is selected from the group consisting of water-soluble and/or fat-soluble vitamins, trace and/or macro minerals, amino acids as well as mixtures thereof.

Particularly suitable fat-soluble vitamins according to the present invention encompass vitamin A, vitamin D3, vitamin E, and vitamin K, e.g. vitamin K3. Particularly suitable water-soluble vitamins encompass vitamin B12, biotin and choline, vitamin B1, vitamin B2, vitamin B6, niacin, folic acid and panthothenate, e.g. Ca-D-panthothenate as well as mixtures thereof.

Particularly suitable trace minerals according to the present invention encompass manganese (e.g. in the form of manganese oxide), zinc (e.g. in the form of zinc oxide), iron (e.g. in the form of iron sulphate), copper (e.g. in the form of copper sulphate), iodine (e.g. in the form of sodium iodine), selenium, and cobalt as well as mixtures thereof.

Particularly suitable macro minerals according to the present invention encompass calcium (e.g. in the form of limestone and calcium (mono, di or triphosphate), magnesium, phosphorus and sodium (e.g. in the form of sodium chloride) as well as mixtures thereof.

In a particular preferred embodiment, the at least one feed ingredient is selected from the group consisting of roughage and concentrates as well as mixtures thereof.

In one particular advantageous embodiment according to the present invention, the storage stable mixture (1) or (1') according to the present invention is a premix (1A) consisting essentially of the ingredients (a1) and (a2).

In a further preferred embodiment, the storage stable mixture (1) is a premix (1B) consisting essentially of
(a1) at least 5 wt.-%, preferably from 5 to 85 wt.-%, most preferably from 5 to 60 wt.-%, based on the total weight of the premix, of a powderous formulation (A), (B), (C), (D), (E), (F) or (G), and
(a2) at least 10 wt.-%, preferably from of 15 to 95 wt.-%, most preferably from 40 to 95 wt.-%, based on the total weight of the premix, of at least one inorganic carbonate.

In another preferred embodiment, the storage stable mixture (2) according to the present invention is a premix (2A) consisting essentially of (a1) to (a3) and optionally (a4) and wherein (a3) is at least one additional active ingredient selected from the group consisting of water-soluble and/or fat-soluble vitamins, trace and/or macro minerals, amino acids as well as mixtures thereof with the proviso that the ingredients (a1) to (a4) sum up to 100 wt.-% t.

In a further preferred embodiment, the storage stable mixture (2) is a premix (2B) consisting essentially of
(a1) at least 5 wt.-%, preferably from 5 to 20 wt.-%, most preferably from 10 to 15 wt.-%, based on the total weight of the premix, of a powderous formulation (A), (B), (C), (D), (E), (F) or (G), and
(a2) at least 10 wt.-%, preferably from of 15 to 70 wt.-%, most preferably from 20 to 50 wt.-%, based on the total weight of the premix, of at least one inorganic carbonate, and
(a3) at least 5 wt.-%, preferably, from 20 to 80 wt.-%, most preferably from 40 to 70 wt-%, based on the total weight of the premix, of at least one active ingredient selected from the group of water-soluble and/or fat-soluble vitamins, trace and/or macro minerals, amino acids as well as mixtures thereof, and
(a4) 0 to 15 wt.-%, preferably 0 to 10 wt.-%, most preferably 0 to 5 wt.-%, based on the total weight of the premix, of at least one edible oil.

It is noted that next to all the preferences given herein, particular preferred edible oils to be used in the storage stable mixtures according to the present invention are corn oil, rapeseed oil, sunflower oil, canola oil and or soy bean oil as well as mixtures thereof, such as most preferably soy bean oil.

The term 'premix' as used herein designates a preferably uniform mixture of the listed ingredients which are generally used to facilitate uniform dispersion of active ingredients into a larger mix.

The term 'premix consisting essentially of' indicates that the addition of all wt-% of the listed ingredients of the premix adds up to 100 wt.-% with the proviso, however, that it cannot be excluded that small amount of impurities or water (moisture) may be present in the powderous formulations according to the present invention such as e.g. in amounts of less than 7 wt.-%, preferably less than 5 wt.-%, more preferably less than 3 wt.-%, which impurities/water (moisture) are introduced via the respective raw materials or processes used and which are not added separately.

All the above disclosed premixes can be used as such or admixed to feed products.

Additionally, all the above disclosed premixes can be used in the production of feed products.

It is well understood, that the storage stable mixture (1) according to the present invention may also be a feed product.

Thus, in another preferred embodiment, the storage stable mixture (2) according to the present invention is a feed product (2a) consisting essentially of (a1) to (a3) and optionally (a4) and wherein (a3) is (a3/1) at least one additional active ingredient selected from the group consisting of water-soluble and/or fat-soluble vitamins, trace and/or macro minerals, amino acids as well as mixtures thereof and (a3/2) at least one feed ingredient selected from the group of roughage and concentrate.

In a further preferred embodiment, the storage stable mixture (2) is a feed product (2b) consisting essentially of
(a1) at least 0.001 wt.-%, preferably from 0.001 to 10 wt.-%, most preferably from 0.001 to 5 wt.-%, based on the total weight of the feed product, of a powderous formulation (A), (B), (C), (D), (E), (F) or (G), and
(a2) at least 1 wt.-%, preferably from of 1 to 20 wt.-%, most preferably from 1 to 10 wt.-%, based on the total weight of the feed product, of at least one inorganic carbonate, and
(a3/1) at least 0.1 wt.-%, preferably from 0.5 to 20 wt.-%, most preferably from 0.5 to 10 wt-%, based on the total weight of the feed product, of at least one active ingredient selected from the group of water-soluble and/or fat-soluble vitamins, trace and/or macro minerals, amino acids as well as mixtures thereof, and
(a3/2) at least 5 wt.-%, preferably from 10 to 95 wt.-%, preferably from 20 to 90 wt-%, based on the total weight of the feed product, of at least one feed ingredient selected from the group of roughage and concentrate as well as mixtures thereof, and
(a4) 0 to 15 wt.-%, preferably 0 to 10 wt.-%, most preferably 0 to 5 wt.-%, based on the total weight of the feed product, of at least one edible oil.

The term roughage (also known as forage) and concentrate are well known to a person skilled in the art. Roughage is primarily composed of cellulosic materials such as plant stems and leaves, e.g. hay, introduced grass, native grass, green roughage, straw, tree leaves, etc.; brans such as rice bran, etc. as well as crude fibers such as e.g. brewery's byproducts. The concentrates are generally comprised of the conventional components such as mainly proteins, starch and fats. The concentrate components thus include, for example cereals such as corn, wheat, barley, rye, oat, wheat flour etc.; oil meals such as soybean meal, sunflower oil meal, etc.; feeds of animal origin such as fish meal, mead-and-bone meal, animal oils (e.g. beef oil, lard oil, bone oil, etc.) without being limited thereto.

In another embodiment, the invention relates to the use of an inorganic carbonate to enhance the retention (i.e. reduce the evaporation) of a compound of formula (I) in a powderous formulation according to the present invention such as in particular in the powderous formulations (A), (B), (C), (D), (E), (F) or (G). Preferably, the retention is at least 70%, preferably at least 80%, more preferably 85%, most preferably at least 90% such as in particular at least 95%.

In another embodiment, the present invention relates to a method of improving the retention (i.e. reducing the evaporation) of a compound of formula (I) in a powderous formulation according to the present invention, said method comprising admixing the powderous formulation with an inorganic carbonate. In a preferred embodiment, the ratio (w/w) of the at least one inorganic carbonate (total) to the powderous formulation is selected in the range of 50:1 to 1:5, preferably in the range of 40:1 to 1:2, most preferably in the range of 30:1 to 1:1 or 20:1 to 1:1, as these formulations are particular suitable to effectively retain the compound of formula (I) over storage.

In another embodiment, the present invention relates to a method of improving the retention (i.e. reducing the evaporation) of a compound of formula (I) in a powderous formulation according to the present invention such as in particular in the powderous formulations (A), (B), (C), (D), (E), (F) or (G), said method comprising the step of preparing a mixture or a premix according to the present invention with all the definitions and preferences as given herein. Preferably, the mixture/premix exhibits a retention of at least 80%, preferably at least 85% most preferably at least 90% such as in particular at least 95%.

The term 'retention' as used therein refers to a retention of the compound of formula (I) with all the definitions and preferences as given herein over a storage time of at least 4 weeks (reclosed (i.e. a bag which has been rolled twice for closure and then fixated with a clip) PE or aluminium bag; 25° C.; 50% relative humidity (r.H.)).

In a further advantageous embodiment, the invention relates to a method to enhance the retention of a compound of formula (I) in a powderous formulation according to the present invention and with all the definitions and preferences as given herein in a feed product, said method comprising the step of adding a mixture according to the present invention with all the definitions and preferences as given herein with/to the feed product.

In a further embodiment, the invention relates to a method to enhance the storage stability of a feed product comprising a powderous formulation according to the present invention such as in particular the powderous formulations (A), (B), (C), (D), (E), (F) or (G), said method comprising the step of adding at least one inorganic carbonate to the feed composition. Preferably, the ratio (w/w) of the at least one inorganic carbonate (total) to the powderous formulation is selected in the range of 50:1 to 1:5, preferably in the range of 40:1 to 1:2, most preferably in the range of 30:1 to 1:1 or 20:1 to 1:1, as these formulations are particular suitable to effectively retain the compound of formula (I) during storage.

Preferably, the amount of the mixture according to the present invention in the feed product is selected such, that the amount of the compound of formula (I) is in the range of 0.01 to 50 g/kg of feed product, preferably in the range of 0.02 to 25 g/kg of feed product, most preferably in the range of 1 to 10 g/kg of feed product.

The term feed product refers in particular to ruminant feed compositions as well as to feed additives.

It is well understood that all the definitions and preferences of the inorganic cabronate, powderous formulations, compounds of formula (I), active and/or feed ingredients and edible oils etc. as given herein also apply to the mixtures, premixes, feed products, uses and methods according to the present invention as outlined above.

The invention is illustrated by the following Examples. All temperatures are given in ° C. and all parts and percentages are related to weight.

EXAMPLES

General Information

A.) HPLC Method

Agilent High Performance Liquid Chromatography 1260 Infinity system, using an Aquasil C18, 150×3 mm, 3 μm column and detecting at 210 nm. The column oven was set to 23° C., the autosampler not temperature controlled. The mobile phase consisted of mobile phase A (940 mL Milli-Q-water+60 ml acetonitrile+1 mL methane sulfonic acid) and mobile phase B (800 ml Milli-Q-water+200 ml acetonitrile+1 mL methane sulfonic acid) which were used in gradient mode (0 min: 0% B, 15 min: 0% B, 15.5 min: 100% B, 21 min: 100% B, 21.5 min: 0% B, 25 min: 0% B (=end of run)) with a flow of 0.4 ml/min.

B.) Powderous Formulation Comprising Propanediol Mononitrate (PF-PDMN)

To 80 g of silica (Newsil C50) placed on a beaker, are added 80 g of a 20 wt.-% mononitrate (PDMN) solution in propyleneglycol under gentle agitation at room temperature. After 5 minutes agitation, the adsorption is completed and a free-flowing powder is obtained.

Example 1: Retention of PDMN in PF-PDMN Admixed with Different Inorganic Carriers 10 g of PF-PDMN and 90 g of an inorganic carrier as outlined in table 1 have been mixed with a TURBULA® Shaker-Mixer (64 rotations/min) for 10 min, sieved through a 2 mm sieve and mixed again for 10 min to obtain homogenous mixtures (100 g batches). Then 10 g of the respective mixtures were stored in reclosed PE bags at 25° C. under controlled atmosphere (50% r.H) for 1 month. Afterwards the remaining content of PDMN was determined by HPLC. The results (as relative concentration to the initial value set to 100%) are presented Table 1.

TABLE 1

Retention of PDMN in PF-PDMN in dependence of various inorganic carriers

| # | Inorganic carrier | Retention [%] |
|---|---|---|
| Inv 1 | Sodium bicarbonate | 65 |
| Inv 2 | Limestone | 62 |
| Ref 1 | Sodium chloride | 47 |
| Ref 2 | Zeolith | 45 |
| Ref 3 | Diatomaceous earth (Kieselgur) | 31 |

As can be retrieved from table 1, the use of the inorganic carbonate according to the present invention resulted in an improved retention of the active compared to other inorganic carriers commonly used in the feed industry.

Example 2: Retention of PDMN in PF-PDMN Admixed with Different Carriers 11 g of PF-PDMN and 11 g of the respective inorganic carrier as outlined in table 2 have been mixed with a TURBULA® Shaker-Mixer (64 rotations/min) for 10 min, sieved through a 2 mm sieve and mixed again for 10 min to obtain homogenous mixtures (22 g batches). Then two samples (5 g each) of the respective mixtures were stored in reclosed PE bags at 40° C. under controlled atmosphere (75% r.H) for 1 week. Afterwards the remaining content of PDMN was determined by HPLC. The results (as relative concentration to the initial value set to 100%) are presented Table 2.

TABLE 2

Retention of PDMN in PF-PDMN admixed with different inorganic carriers in a 1:1 ratio

| # | Organic carrier | Retention [%] |
|---|---|---|
| Inv 3 | Limestone | 94 |
| Ref 4 | Dicalcium phosphate | 88 |

As can be retrieved from table 2, also at lower inorganic carbonate ratios the use the inorganic carbonate resulted in an excellent retention of the active—even under stress conditions (i.e. high temperature and high humidity)—compared to the use of an inorganic phosphate.

The invention claimed is:

1. A storage stable mixture comprising a premix consisting essentially of a uniform mixture of components:
   (a1) at least 5 wt. %, based on the total weight of the mixture, of a powderous formulation comprised of:
   (i) a compound of formula (I):

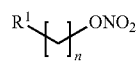

formula (I)

wherein
   n is an integer from 1 to 15
   $R^1$ is selected from the group consisting of H, $C_1$-$C_6$alkyl, phenyl, —OH, —$NH_2$, —CN, —COOH, —O(C═O)$R^8$, —NHC(═O)$R^8$, $SO_2NHR^8$, and —$ONO_2$, and
   $R^8$ is $C_1$-$C_6$alkyl, phenyl, or pyridyl,
   with the proviso that when n is >3 the hydrocarbon chain may be interrupted by —O— or —NH—, and
   (ii) silica, and
   (a2) at least 10 wt. %, based on the total weight of the mixture, of at least one inorganic carbonate, wherein the at least one inorganic carbonate is present in an amount such that a weight ratio (w/w) in the premix of the at least one inorganic carbonate to the compound of formula (I) is at least 50:1 sufficient to achieve storage stability of the uniform mixture of the components (a1) and (a2) such that retention of the compound of formula (I) is improved by at least 10% when stored in a closed container for 1 month at 25° C. and 50% relative humidity as compared to a mixture which does not include the at least one inorganic carbonate of the component (a2).

2. The storage stable mixture according to claim 1, wherein the compound according to formula (I) is propanediol mononitrate.

3. The storage stable mixture according to claim 1, wherein the at least one inorganic carbonate is selected from the group consisting of calcium carbonate, magnesium carbonate, sodium hydrogen carbonate and mixtures thereof.

4. The storage stable mixture according to claim 1, wherein the weight ratio (w/w) of the at least one inorganic carbonate to the compound of formula (I) is in a range of 50:1 to 100:1.

5. The storage stable mixture according to claim 1, wherein the component (a1) of the powderous formulation consists essentially of:
   (i) 2 to 20 wt. %, based on the total weight of the powderous formulation, of the compound of formula (I),
   (iii) at least 25 wt. %, based on the total weight of the powderous formulation, of the silica,
   (iv) 10 wt. % to 45 wt. %, based on the total weight of the powderous formulation, of an edible oil, and
   (v) 0 to 10 wt. %, based on the total weight of the powderous formulation, of an additive.

6. The storage stable mixture according to claim 5, wherein the edible oil in the powderous formulation is selected from the group consisting of propyleneglycol, canola oil, corn oil, rapeseed oil, sunflower oil, medium chain triglyceride (MCT), glycerol and mixtures thereof.

7. The storage stable mixture according to claim 5, wherein the additive comprises at least one thickener selected from the group consisting of gums and cellulose derivatives.

8. The storage stable mixture according to claim 5, wherein the edible oil is propyleneglycol.

9. The storage stable mixture according to claim 2, wherein the component (a1) of the powderous formulation consists essentially of:
   (i) 2 to 15 wt. %, based on the total weight of the powderous formulation, of the propanediol mononitrate,
   (ii) at least 45 wt. %, based on the total weight of the powderous formulation, of the silica, and
   (iii) 20 to 40 wt. %, based on the total weight of the powderous formulation, of propyleneglycol.

10. The storage stable mixture according to claim 1, wherein the premix further consists essentially of components:
    (a3) at least one active ingredient selected from the group consisting of water-soluble vitamins, fat-soluble vitamins, trace minerals, macro minerals, amino acids and mixtures thereof, and optionally
    (a4) at least one edible oil,
    with the proviso that the amount of components (a1) to (a4) sum up to 100 wt. %.

11. The storage stable mixture according to claim 1, wherein the mixture is a feed product further comprising components:
    (a3/1) at least one active ingredient selected from the group consisting of water-soluble vitamins, fat-soluble vitamins, trace minerals, macro minerals, amino acids and mixtures thereof,
    (a3/2) at least one feed ingredient selected from the group consisting of roughage and concentrates, and optionally
    (a4) at least one edible oil.

12. The storage stable mixture according to claim 1, wherein $R^8$ is 2-pyridyl.

13. The storage stable mixture according to claim 1, wherein the at least one inorganic carbonate is selected from the group consisting of calcium carbonate, sodium bicarbonate and mixtures thereof.

14. The storage stable mixture according to claim 4, wherein the weight ratio (w/w) of the at least one inorganic carbonate to the compound of formula (I) is in a range of 75:1 to 100:1.

15. The storage stable mixture according to claim 5, wherein the additive comprises at least one thickener selected from the group consisting of xanthan gum, karaya gum and ethylcellulose.

\* \* \* \* \*